United States Patent [19]

Abbott

[11] Patent Number: 4,657,490

[45] Date of Patent: Apr. 14, 1987

[54] INFUSION PUMP WITH DISPOSABLE CASSETTE

[75] Inventor: Martyn S. Abbott, Richardson, Tex.

[73] Assignee: Quest Medical, Inc., Carrollton, Tex.

[21] Appl. No.: 717,131

[22] Filed: Mar. 27, 1985

[51] Int. Cl.$^4$ .......................... F04B 43/08; A61M 1/00
[52] U.S. Cl. ..................................... 417/478; 417/479;
  417/505; 604/153; 92/101
[58] Field of Search ................... 92/101; 417/244, 254,
  417/267, 412, 413, 317, 505, 510, 474, 475, 478,
  479; 604/153

[56] References Cited

U.S. PATENT DOCUMENTS

| | | | |
|---|---|---|---|
| 9,107 | 7/1852 | Ware | 92/101 |
| 936,089 | 10/1909 | Wise et al. | 417/244 |
| 1,305,603 | 6/1919 | Hodgson | 92/101 |
| 1,338,081 | 4/1921 | Hodgson | 92/101 |
| 2,961,965 | 11/1960 | Senning et al. | 103/37 |
| 4,199,307 | 4/1980 | Jassawalla | 417/474 |
| 4,236,880 | 12/1980 | Archibald | 417/478 |
| 4,273,121 | 6/1981 | Jassawalla | 128/214 F |
| 4,276,004 | 6/1981 | Hahn | 604/153 |
| 4,277,226 | 7/1981 | Archibald | 604/153 |
| 4,322,201 | 3/1982 | Archibald | 417/279 |
| 4,335,835 | 6/1982 | Biegler et al. | 222/95 |
| 4,468,222 | 8/1984 | Lundquist | 604/153 |
| 4,479,760 | 10/1984 | Bilstad | 604/153 |
| 4,548,607 | 10/1985 | Harris | 604/153 |

FOREIGN PATENT DOCUMENTS

| | | | |
|---|---|---|---|
| 1911919 | 3/1969 | Fed. Rep. of Germany | |
| 201375 | 11/1936 | Sweden | 92/101 |
| 2053378 | 2/1981 | United Kingdom | |

Primary Examiner—Carlton R. Croyle
Assistant Examiner—Paul F. Neils
Attorney, Agent, or Firm—Roger C. Clapp

[57] ABSTRACT

An infusion pump incorporates a cassette formed by bonding of two substantially flat sheets. The fluid to be infused to the patient comes into contact only with the cassette. The cassette includes first and second flexible sheets which define a pumping chamber therebetween. The infusion pump is provided with a pumping member having a hub and a plurality of petal-shaped sections extending radially outward therefrom and pivotal relative thereto. A stepping motor can be operated to move the pumping member against the second flexible sheet to decrease the volume of the pumping chamber and pump fluid to the patient. A load cell monitors the force exerted by the stepping motor on the hub. An outlet restriction valve is electronically controlled by a second stepping motor in response to the pressure sensed by the load cell to control pumping to a predetermined pressure. The pressure can be selectively varied which permits the use of a low pressure at low flow rates to decrease the time necessary to detect an occlusion in the output line.

13 Claims, 11 Drawing Figures

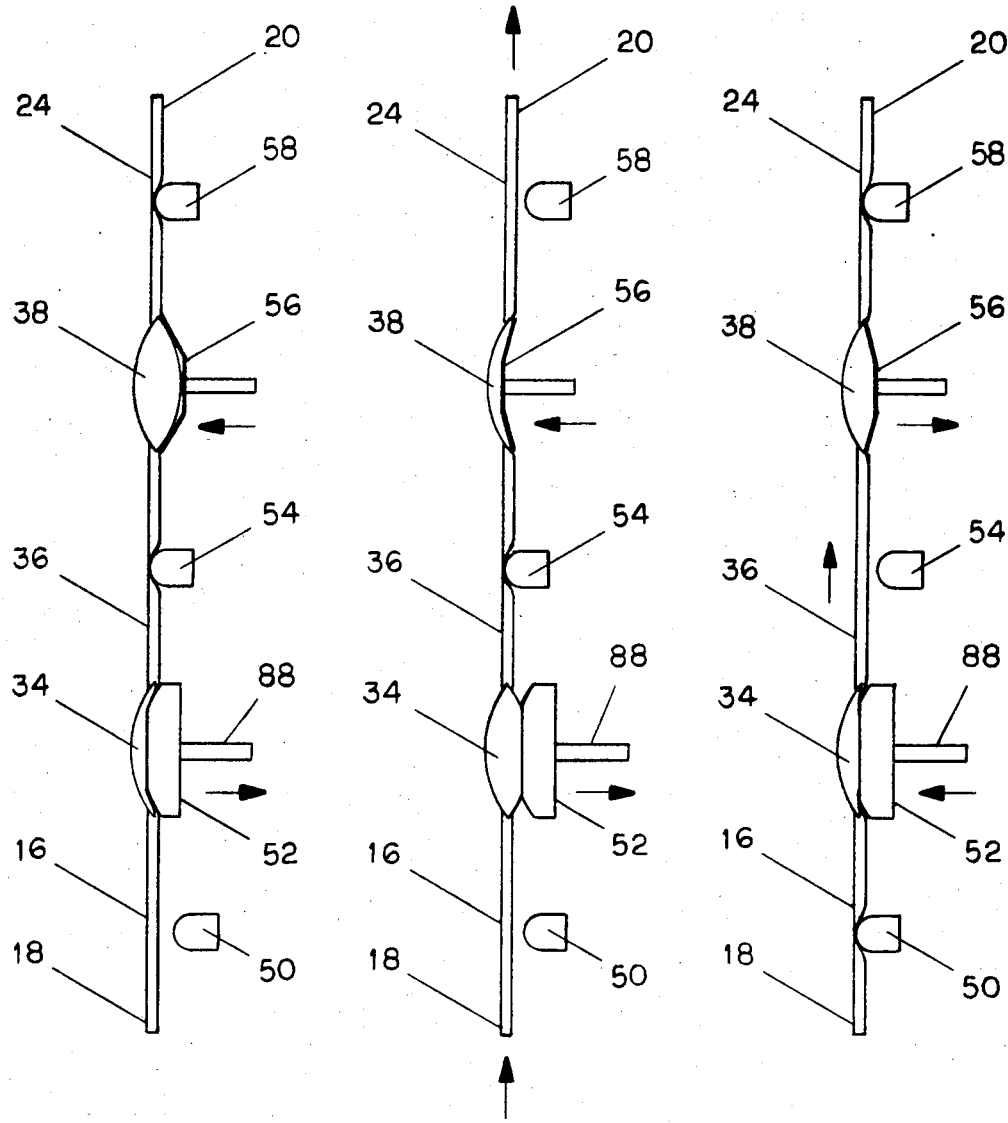

INFUSION PUMP WITH DISPOSABLE CASSETTE

TECHNICAL FIELD

This invention relates to the delivery of a fluid to a patient by pressurizing the fluid, and in particular to delivery by an infusion pump which incorporates an inexpensive disposable cassette.

BACKGROUND OF THE INVENTION

Infusion of fluids, such as drugs and plasma, into a patient is commonplace in the medical field. Two common infusion methods are intravenous delivery of fluids by gravity and either intravenous or intraarterial delivery by actually pumping the fluids for delivery to the patient.

In pump delivery, an infusion pump is used to pressurize the fluid. Past devices often require a complex cassette mechanism which comes into direct contact with the fluid to be delivered.

However, peristaltic pumps acting upon in-line tubing segments have been used in this art. One example of a peristaltic pump, disclosed in U.S. Pat. No. 4,155,362, includes a back pressure valve to prevent gravity siphoning from the pumping chamber.

Another relatively simple pumping arrangement is disclosed in U.S. Pat. No. 4,142,524, in which a casette is provided with inlet and outlet valves to and from a pumping chamber. The pump presses a rubber diaphragm on the cassette to diminish the volume of the casette chamber by a known amount to deliver a predetermined quantity per pump stroke. An even simpler disposable element is disclosed in the pumping arrangement of U.S. Pat. No. 4,199,307, in which a pancake-shaped resilient pumping chamber is provided with upper and lower valves and an activating pumping piston which displaces a known volume on the pumping stroke. Yet another pump approach is disclosed in U.S. Pat. No. 4,322,201, which seeks to provide continuous, uninterrupted fluid flow by alternating between two pumping chambers, each of which employs the principle of the rolling diaphragm. A third rolling diaphragm chamber is employed for mechanically sensing pressure within the device for control purposes.

None of the foregoing art, however, possesses the advantages of the present invention in providing an extremely simple disposable element in combination with a relatively straightforward pumping action which is accurate and which provides sound and reliable pressure monitoring and self-checking diagnostics.

SUMMARY OF THE INVENTION

In accordance with one aspect of the present invention, an infusion pump is provided for pumping a fluid to a patient for infusion. The pump includes a disposable cassette having first and second flat flexible sheets defining a pump chamber within the cassette, the pump chamber being variable in volume as fluid fills the chamber or is pushed from it, the disposable cassette further having an inlet passage for movement of fluid into the pump chamber and an outlet passage for movement of the fluid out of the pump chamber. Means are provided for confining movement of the outer surface of the first sheet; and a pumping member is provided for contacting the outer surface of the second sheet to deform the sheet between the pumping member and the confining means to decrease the volume of the pump chamber and pump the fluid from the pumping chamber. The pumping member includes a center hub section and individual petal-shaped sections pivotally attached to the hub and extending radially outward from the hub. Means are provided for supporting each of the petal-shaped sections at their remote ends for pivotal motion about an axis generally parallel to the axis of pivotal motion between each petal-shaped section and the hub. Means are provided for urging the hub against the outer surface of the second sheet with the petal-shaped sections pivoting about the axes and also being urged against the second sheet. Substantially the entire surface area of the second sheet is contacted by the hub and petal-shaped sections to decrease the volume of the pumping chamber and pump the fluid therefrom.

In accordance with another aspect of the present invention, the structure for confining the first sheet comprises a concave curved surface of constant radius against which the outer surface of the first sheet is confined. Also, an inlet valve can be provided for opening and closing the inlet passage in the cassette and a delivery valve is provided for closing the outlet passage to a variable orifice size so that the valve opens to permit fluid flow from the pump chamber past the outlet valve when the movement of the pump piston pressurizes the fluid in the pumping chamber to a predetermined pressure. The outlet valve can be electronically controlled to allow the pressure in the pump chamber to be automatically controlled in a predetermined manner, as by controlling it to a constant pressure level selected by the user. A load cell may be used to measure the fluid pressure in the pump chamber and can detect a lack of fluid, valve failure and occlusions.

In accordance with another aspect of the present invention, the disposable cassette is provided with a quick-fill supply chamber upstream from the pumping chamber. An inlet passage is provided for movement of fluid into the supply chamber and a valve supply transfer passage is provided for movement of the fluid from the supply chamber to the pump chamber.

BRIEF DESCRIPTION OF THE DRAWINGS

A more complete understanding of the invention may be had by reference to the following Detailed Description when taken in conjunction with the accompanying Drawings, wherein:

FIGS. 8, 9 and 10 illustrate schematically the operational sequence of the infusion pump.

DETAILED DESCRIPTION

Figure 1:
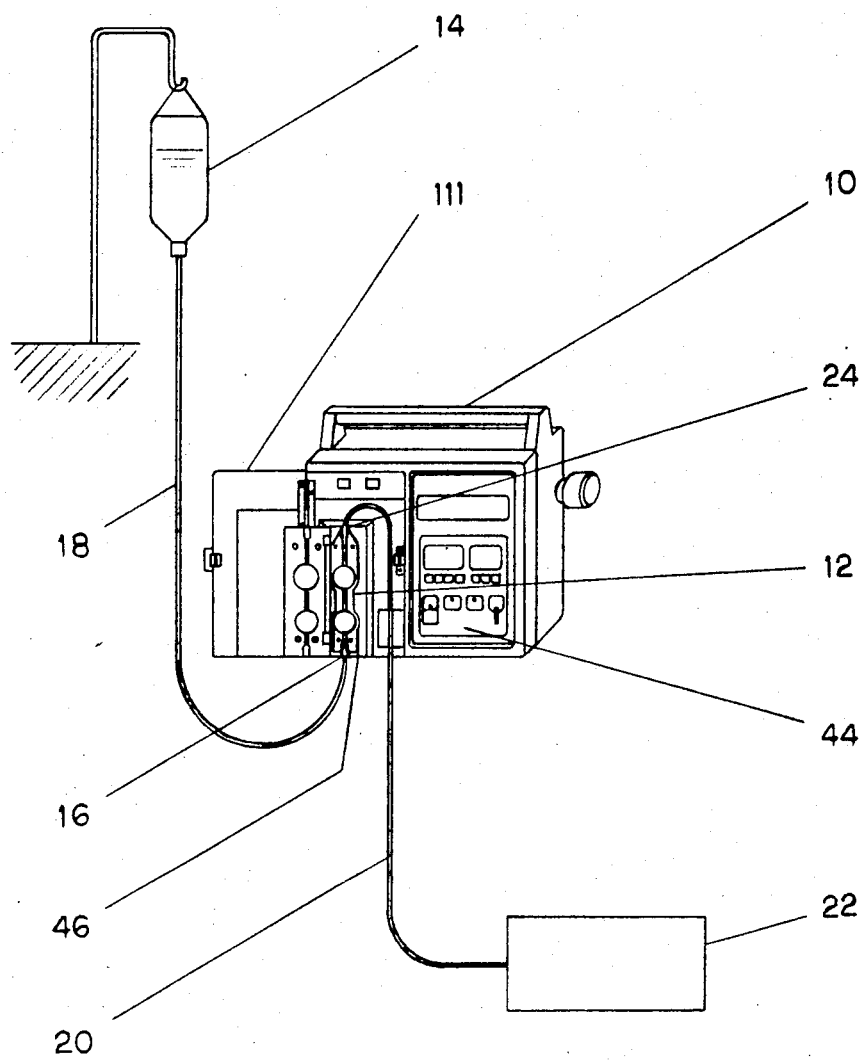
FIG. 1 is a schematic representation of an infusion pump forming one embodiment of the present invention.

As illustrated in FIG. 1, the pumping system is composed of an instrument 10 in which a disposable cassette 12 is mounted for operation. Supply container 14 containing the fluid to be infused is connected to inlet 16 of the cassette 12 by means of tubing 18. Outlet tubing 20 extends to the patient 22 from the outlet 24 of cassette 12.

Figures 4, 5:
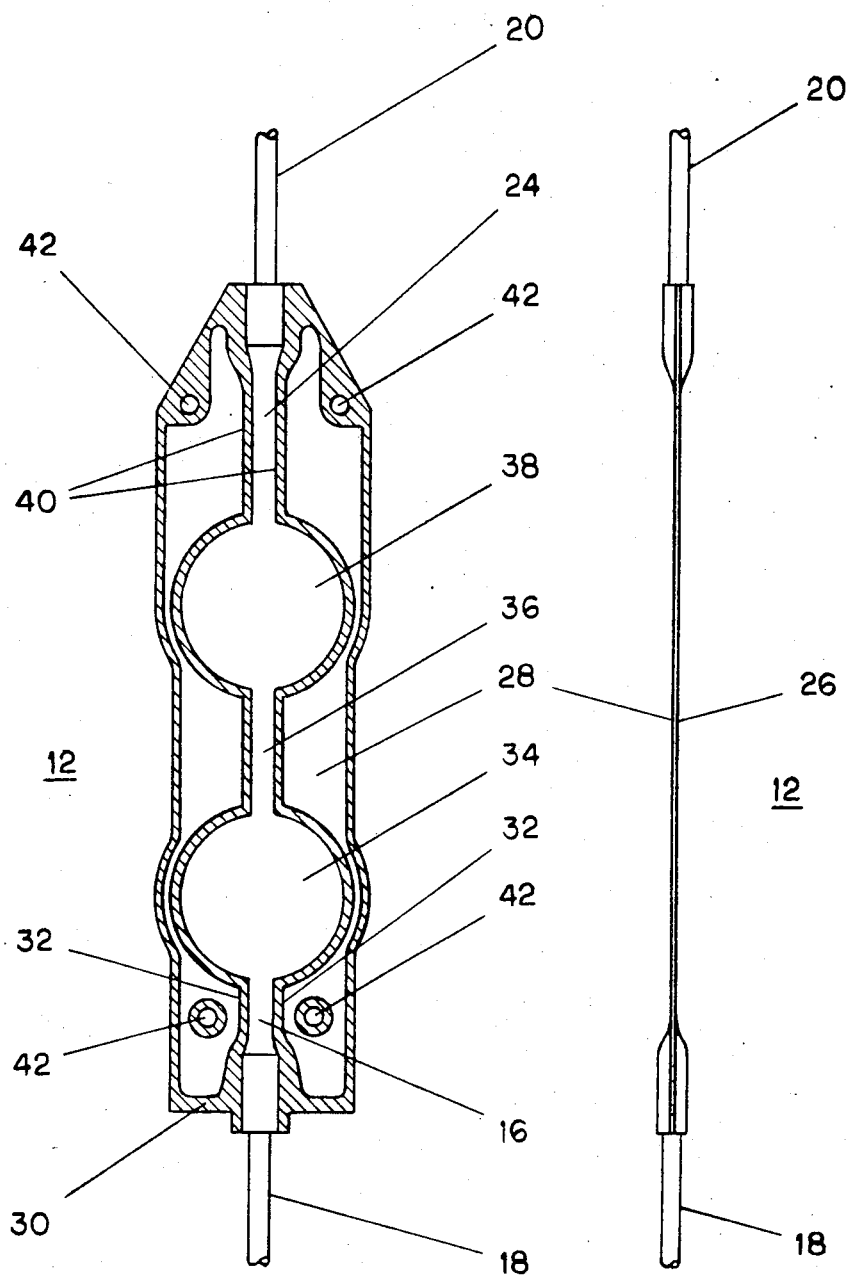
FIG. 4 is a front view of the disposable cassette.
FIG. 5 is a side view of the disposable cassette.

Cassette 12, as best seen in FIGS. 4 and 5, is formed by a first flexible sheet 26 and a second flexible sheet 28, which may be formed from a suitable flexible sheet material, such as polyvinyl chloride. The cassette 12 may be assembled by bonding sheets 26 and 28 over a selected bonding area 30 indicated by hatching in FIG. 4. The bonding area 30 includes bonding along spaced parallel lines 32 in order to form a cassette inlet passage 16 extending from one end of the cassette between sheets 26 and 28. Inlet passage 16 extends to a supply chamber 34 having a generally circular configuration. A transfer passage 36 extends from the side of supply chamber 34 opposite inlet passage 16, communicating with a pump chamber 38. Bonding along two parallel lines 40, extending from pump chamber 38 forms outlet passage 24.

Thus, there is provided longitudinally through the central area of cassette 12, a continuous fluid path extending from inlet 16 through supply chamber 34, transfer passage 36, and pump chamber 38 to the cassette outlet 24. Supply tube 18 is inserted into inlet passage 16 and bonded by any suitable means, such as by solvent bonding. Likewise, patient tube 20 is inserted into outlet passage 24 and bonded thereto. In the preferred form of the invention, the cassette is, as shown in FIG. 5, essentially flat. This permits production of the cassette from flat sheet without the necessity of any forming operation. Depending upon the material used for sheets 26 and 28, it may be desirable to provide slight relief by vacuum forming in one or both of the sheets along the open flow path formed by the cassette, in order to minimize adhesion of the unbonded areas during storage.

The flexibility of the cassette must be sufficient that, with fluid at a relatively low pressure being provided at the inlet 16, with the outlet 24 closed, fluid will flow into the cassette filling it and causing the chamber 34 and 38 to bulge with fluid by stretching of the sheets 26 and 28. Four mounting holes 42 are provided in the margins of the cassette for positioning and mounting of the cassette in the instrument 10.

Figure 2:
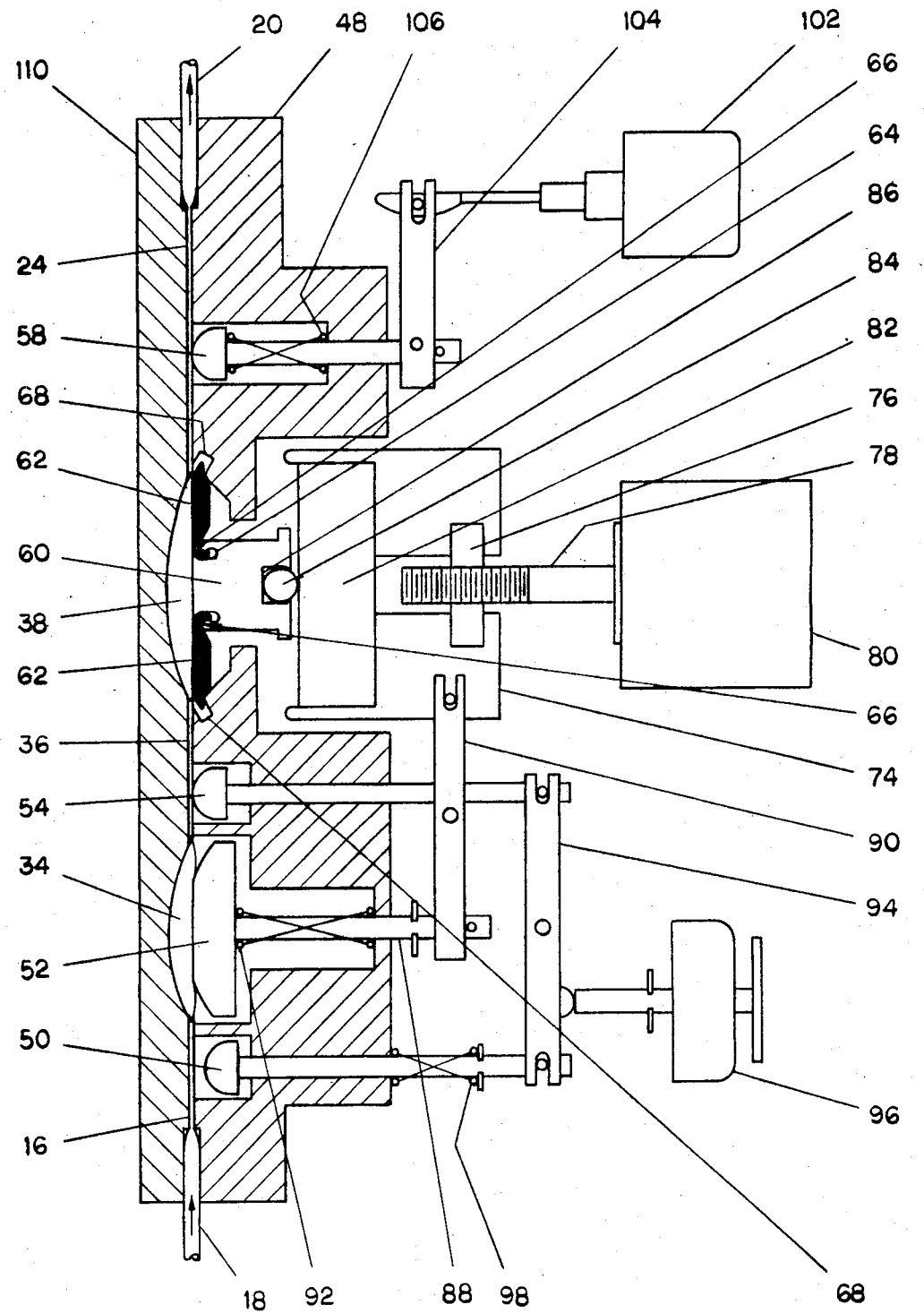
FIG. 2 is a cross-sectional view of the infusion pump taken along the line 2—2 in FIG. 1.
Figure 3:
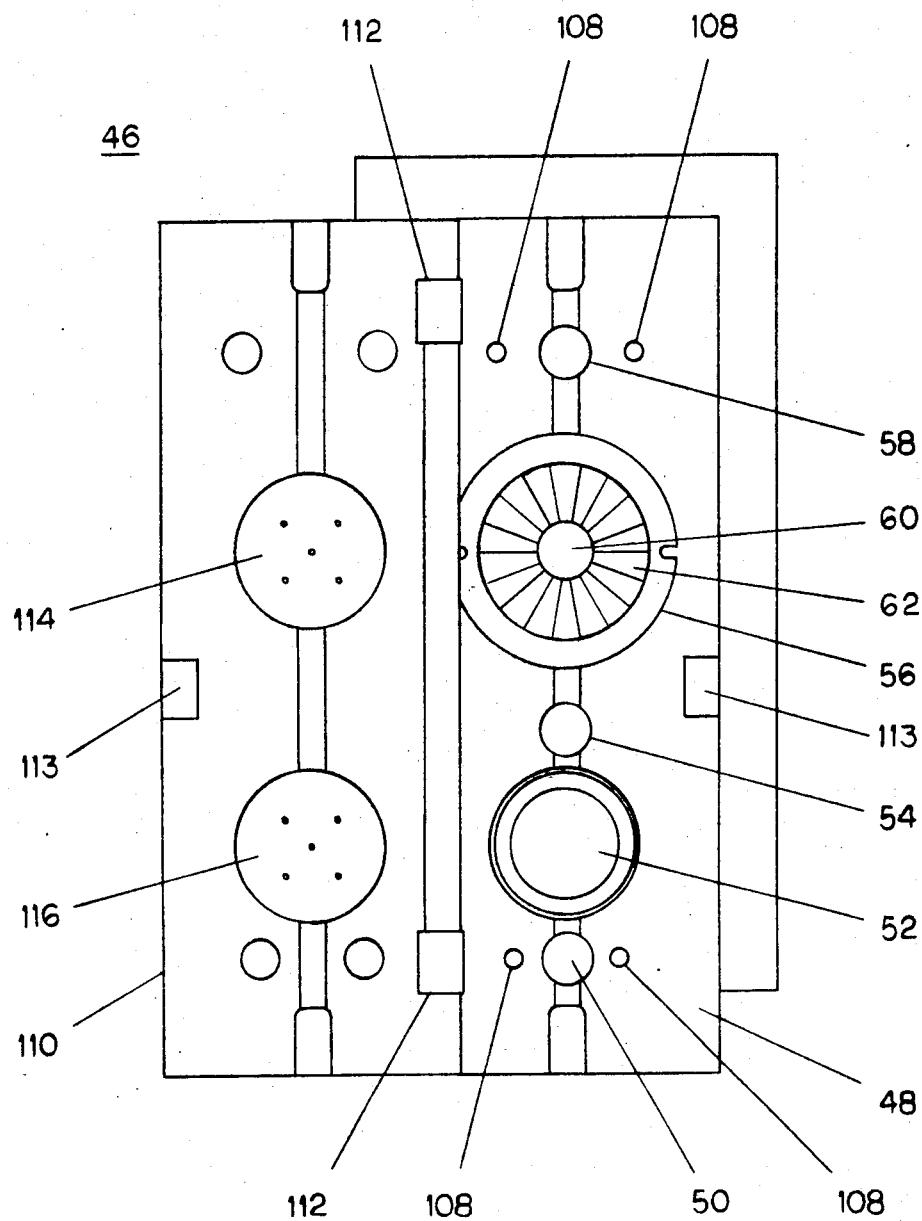
FIG. 3 is a front view of the pump prior to mounting the disposable cassette.

The front panel of the instrument body is functionally divided into a data display/operator input panel 44 and a cassette receiving and actuating section 46, which is concealed behind one or more doors (not shown in FIG. 1). The details of construction of the cassette receiver/actuator section 46 are best illustrated in FIGS. 2 and 3. The moving members which operate upon cassette 12 when it is in operating position are arrayed on panel 48 secured to the instrument body. Proceding from upstream, the major elements are: inlet valve 50, refill pressure member 52, transfer valve 54, petal assembly pumping member 56, and delivery valve 58.

Figure 6:
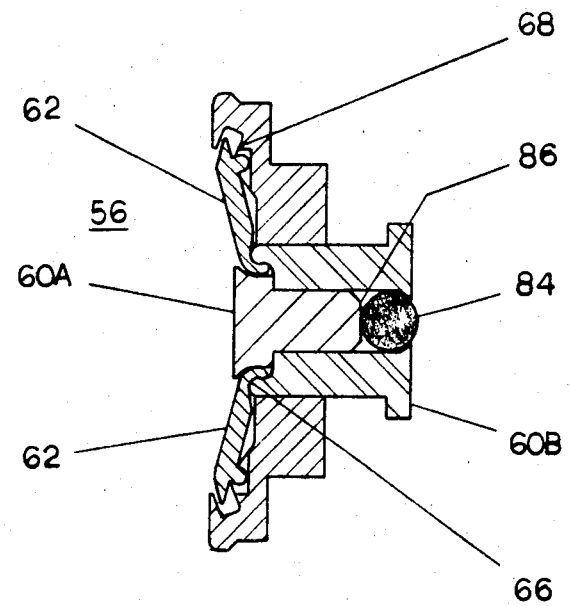
FIG. 6 is a partial cross-sectional view of the pumping member shown in the retracted position.
Figure 7:
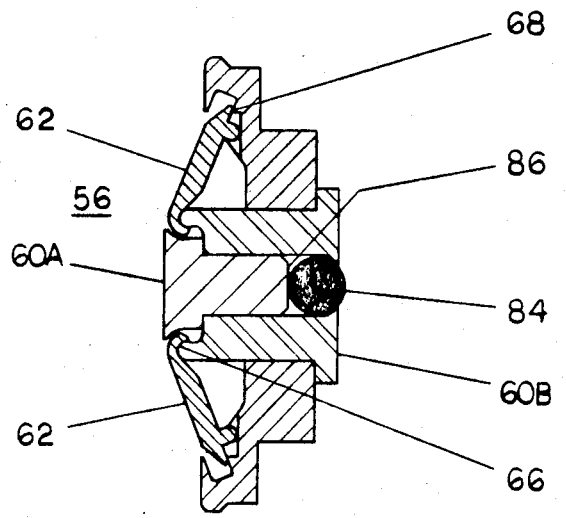
FIG. 7 is a partial cross-sectional view showing the pumping member of the infusion pump in the extended position.

Petal assembly 56 includes a central hub 60 surrounded by a plurality of petal shaped sections 62 to form the movable pressing surface which produces pumping pressure in the device. As best shown in FIGS. 6 and 7, the hub 60 is formed by press fit of male hub member 60a and female hub member 60b. A circular recess 64 near the outer edge of hub 60 is formed between the two hub members. Each petal section 62 is provided on the rear face of its inner end with a smooth hooked-shape curve portion 66 which corresponds to a smooth curve provided on the hub recess 64. The inner end of each petal section 62 is pivotally retained in the hub recess 64, with the complimentary smooth curves of each member permitting relative pivotal movement of each petal shaped section with respect to the hub about an axis adjacent recess 64. The instrument body panel 48 is provided with an annular petal nest 68 that circumferentially surrounds hub 60 and retains the outer end of each petal shaped section 62. The confronting surfaces of petal nest recess 68 and the outer end of each petal shaped section 62 are also shaped for smooth pivoting of the petal shaped sections with respect to the instrument body about an axis adjacent the nest 68.

A movable carriage 74 is mounted behind hub 60, and carries a drive nut 76 which is engaged with the threads of a threaded motor shaft 78 rotated by stepper motor 80. The forward end of carriage 74 is recessed to receive a load cell 82. Load cell 82 has its central force-measuring diaphragm confronting a metal ball 84 retained in a rear central recess 86 formed on hub 60. Thus, rotation of stepper motor 80 acts, through the cooperation of threaded motor shaft 78 and carriage nut 76 to drive carriage 74 forward. This action transmits force through load cell 82 and metal ball 84 to hub 60, moving the hub forward. The translational motion of hub 60 also causes each petal shaped section 62 to pivot near each of its ends. The petal assembly thus forms a truncated cone of varying height as the hub moves between the extreme positions illustrated in FIGS. 6 and 7.

Refill pressure member 52 is carried at the forward end of refill shaft 88, which is driven either forwardly or rearwardly through lever 90 acted upon by the carriage 74. Thus, as viewed in FIG. 2, when carriage 74 is moving forwardly to push the petal assembly 56 forward, the action of refill lever 90 causes shaft 88 and refill pressure member 52 to be withdrawn. As motor 18 is driven in the opposite direction to withdraw carriage 74, lever 90 allows the refill pressure member 52 to move forward. Spring 92 biases refill pressure member 52 to its forward position, and thus carriage 74 to the rearward direction.

Inlet valve 50 and transfer valve 54 have rounded surfaces for engaging the flow path of the cassette, and are operated in tandem fashion through inlet valve lever 94 driven by solenoid 96. When one of the two valves is in the open or rearward position, the other is necessarily in the closed or forward position. Preferably, the parts are assembled so that in the middle of the path of travel of valve lever 94, both valves are closed to ensure no by-passing of fluid. Bias to inlet valve lever 94 is provided by spring 98 surrounding the inlet valve shaft, which biases the arrangement to the condition of inlet valve open, transfer valve closed.

Delivery valve 58 is operated by a stepper motor 102 acting through delivery valve lever 104, and is biased to the closed position by spring 106. The linear stepper motor 102 is capable of positioning the delivery restriction valve 58 in any position from fully retracted or open position, as shown, to a fully extended or closed position.

Actuator panel 48 is provided with mounting pins 108 corresponding to the mounting holes 42 in cassette 12. An actuator door 110 is mounted to panel 48 by hinges 112 and is closed by latch 113. Although not shown in FIG. 3, a second outer door 111 (FIG. 1) is preferably used to enclose door 110. As a double check for patient safety, opening of this outer door 111 would stop pumping and sound an alarm. In the inner face of door 110, concave depression 114 is arranged to confront petal assembly 56 when the door is closed, and similar concave depression 116 confronts the refill pressure member 52. Depressions 114 and 116 are provided with air vent holes through the front of the door to facilitate closing of the door with the cassette 12 in position. With the cassette mounted on pins 43, the pump chamber 38 of the cassette is captured between petal assembly 56 and door depression 114. The supply chamber 34 is likewise captured between pressure member 52 and door depression 116. In the operating position, valve 50 is adjacent inlet passage 16 to close off the inlet when valve member 50 is extended. Likewise, valve 54 may be activated to close off transfer passage 36. The delivery valve 58 may be activated to selectively close outlet 24 of cassette 12, to an orifice of any desired size. The pumping compartment defined between the rigid wall of depression 114 and the petal assembly 56 must be completely filled by the fluid filled pump chamber 38 when the petal assembly 56 is in its retracted position illustrated in FIG. 6, and the pump chamber 38 is bulged with fluid at a low fluid pressure of approximately 10 inches of water. The volumetricity of pumping is then provided by the accuracy of volume displaced between the extreme positions of the petal assembly 56 illustrated in FIGS. 6 and 7, and the compliance of sheet 28 to the moving truncated cone surface presented by the petal assembly 56.

Since the material used to construct the cassette is flexible it conforms to the surface of the petal elements so that the position of the petal assembly defines the volume of fluid enclosed between it and the hemispherical surface on the other side very precisely. This enables the volumetric performance of this arrangement to be defined almost completely by the movement of the hub, and thus of the petal shaped sections, and not by the mechanical properties of the disposable element. The volume displaced by the petal assembly varies in a linear fashion with the translational movement of hub 60.

Figure 11:
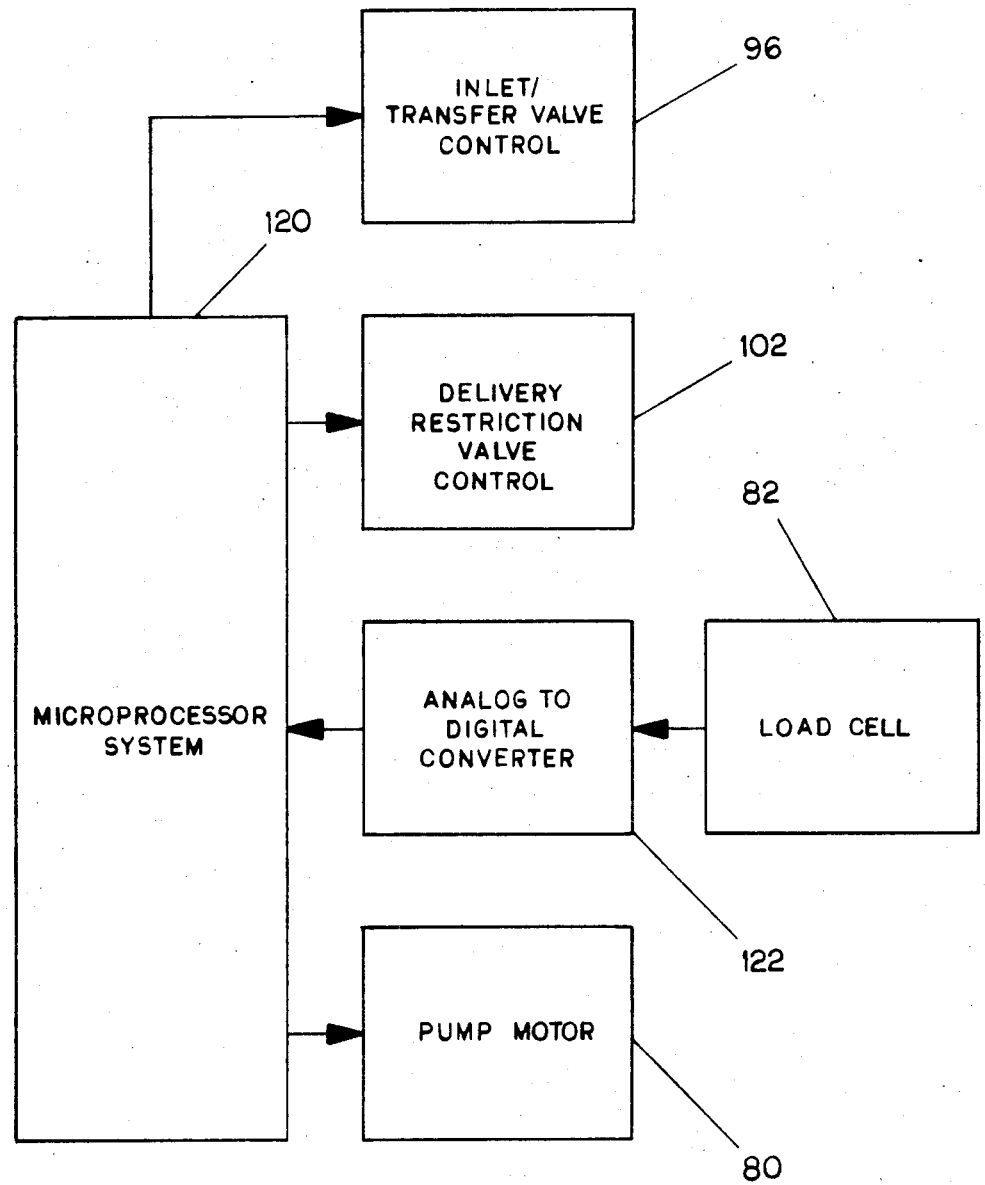
FIG. 11 is a schematic of the electronic controls within the infusion pump.

As illustrated in FIG. 11, the system is operated under the control of a microprocessor system 120. The microprocessor, as illustrated in FIG. 11, controls the movement of solenoid 96 between its two positions: (1) inlet valve open, transfer valve closed, and (2) inlet valve closed, transfer valve open. Likewise, microprocessor 120 controls delivery valve stepper motor 102 to select the total or partial restriction imposed by delivery valve 58 on the cassette outlet 24. Microprocessor 120 also selects, in accordance with the rate selected by the operator on input panel 44, the rate of movement of the pumping stepper motor 80. Continuous control over operation, and diagnostics for abberant conditions, are principally provided by load cell 82 which directly measures the force being exerted on the pump chamber 38 by petal assembly 56. This data is continuously provided to microprocessor 120 through A/D converter 122.

A typical cycle of operation is illustrated in FIGS. 8 through 10. FIG. 8 illustrates the condition of the actuator and disposable as the delivery portion of the cycle has begun. At this stage, the pump chamber 38 has been completely filled with fluid to occupy the compartment with petal assembly 56 fully retracted. Delivery valve 58 and transfer valve 54 are closed, completely capturing the fluid in pump chamber 38. Inlet valve 35 is opened, so that fluid may enter the supply chamber 34 as refill pressure member 52 is retracted. In this initial stage, the microprocessor begins the initial stage of the delivery cycle by directing the pump chamber stepper motor 80 to advance to begin pressurization of the fluid in pump chamber 38. During the first few steps of operation, valves 58 and 54 remain closed to permit this initial pressurization. Elevation of the force required to advance the petal assembly 56 is sensed by load cell 82 which data is fed to the microprocessor 120. This state serves as a diagnostic to verify the capturing of a full load of fluid in the pump chamber 38. A failure to pressurize in the first several steps of motor 80 indicates a system problem. It could be that the fluid supply is depleted, so that the pump chamber 38 has not been filled, or that the supply container 14 is at an inadequate height to cause the gravity fill into inlet 16 of the cassette. A third possibility is that a valve defect in valve 54 or 58 is permitting fluid to leak from the chamber 38. In any of these events, operation of the instrument will be stopped by the microprocessor 120 and an alarm sounded.

If, however, normal pressurization occurs, microprocessor 120 instructs delivery valve 58 to open as motor 80 advances, to deliver fluid to the patient through outlet 24, as illustrated in FIG. 9. Continuous monitoring of load cell 82 permits the microprocessor to exercise continuous control over delivery valve 58 to selectively restrict the outlet 24. This permits the device to ensure that gravity siphoning at a higher rate than the requested rate does not occur. The microprocessor is also programmed with a selected maximum pressure limit set by the user through display/input panel 44, which is used in the continuous pressure monitoring. Escalation of pressure above the selected maximum pressure, even with the delivery valve 58 wide open, will result in alarm and shutdown of the instrument, indicating that there is some occlusion which requires nursing attention, and that fluid is not reaching the patient. The ability to select a maximum pressure limit by the user permits relatively rapid occlusion alarms, even at relatively low selected infusion rates.

Preferably, the microprocessor is programmed to maintain a relatively constant pressure in pump chamber 38 by selective restriction of delivery valve 58, such constant pressure being just below the maximum pumping pressure selected by the operator. This is helpful in ensuring that there are no variations in volumetric delivery which might result from operation at varying pumping pressures.

While fluid is being delivered by advancement of the petal assembly 56, the refill pressure member 52 is automatically being withdrawn, and fluid is entering the supply chamber 34 through open inlet 16. When petal assembly 56 has reached its fully extended position, illustrated in FIG. 7, valves 50 and 58 close, and valve 54 opens. Microprocessor 120 then reverses stepper motor 80 for a rapid retraction of petal assembly 56 and a rapid extension of refill pressure member 52 as illustrated in FIG. 10. This permits a very quick transfer of fluid into pump chamber 38 which will arm the device for the next delivery cycle. During the pumping portion of the delivery cycle energy was stored in the spring 92 immediately behind the refill pressure member 52. This energy is used to effect the transfer of fluid so as to drastically reduce the mechanical loading on the main pump motor. The purpose of this is to allow an increased motor speed during the fluid transfer step which in turn reduces the time taken to effect the transfer as it is principally limited only by the maximum operating speed of the main pump motor 80. Once the transfer of fluid is complete valve 50 opens and valve 54 closes and the system is in the condition once more indicated in FIG. 8. A mechanical stop on shaft 88 limits the amount of movement of the refill piston 52 so as to avoid pumping any fluid back towards the fluid container 14 as valve 50 opens.

It will be appreciated that the cassette and instrument could be designed without supply chamber 34, refill pressure member 52, and transfer valve 54, but in that event the refill cycle time would be dependent upon the rate of flow into pump chamber 38 dictated by natural forces of gravity. Use of the device in the form illustrated permits the instrument to control the time taken up by the refilling of pump chamber 38, and to cause that step to happen rapidly to limit the duration of the refilling cycle.

Although specific embodiments of the invention have been illustrated in the accompanying drawings and described in the foregoing detailed description, it will be understood that the invention is not limited to the embodiments disclosed, but is capable of numerous rearrangements, modifications and substitutions of parts and elements without departing from the spirit of the invention.

I claim:

1. A pump for parenteral administration of fluid to a patient at a selectable rate comprising:
   a flexible cassette formed of a pair of substantially flat flexible sheets defining a flow path between an inlet and an outlet, and a pump chamber located in that flow path;
   an instrument body having a compartment receiving the cassette and confining the pump chamber;
   pumping means associated with the instrument body adjacent the compartment for confining the pump chamber, comprising a moveable hub circumferentially surrounded by radially extending petal-shaped sections each of which is pivotally mounted to the hub at its inner end and to a portion of the instrument body at its outer end; and
   activation means for activating the pumping means to move the hub and the petal-shaped sections into the compartment to reduce the volume of the pump chamber at a rate dependent upon the selected rate.

2. The pump of claim 1, further comprising:
   a supply chamber in the flow path of the cassette between the inlet and the pump chamber,
   refill pressure means carried by the instrument body for movement toward and away from the supply chamber;
   an inlet valve carried by the instrument body adjacent the inlet of the disposable element;
   a transfer valve carried by the instrument body adjacent the flow path between the supply chamber and the pumping chamber;
   a delivery valve carried by the instrument body adjacent the outlet; and
   control means for, at first times, closing the delivery valve and the inlet valve, and opening the transfer valve, and rapidly retracting the pumping means from the pump chamber while rapidly pushing the refill pressure means towards the supply chamber, whereby the pump chamber is rapidly refilled; and, at second times, opening the delivery valve and inlet valve and closing the transfer valve and activating the pumping means to reduce the volume of the pump chamber at a rate determined by the selected delivery rate while retracting the refill pressure means.

3. The pump of claim 1, wherein the disposable element is formed entirely from the joining of two substantially flat plastic sheets, a supply tube is bonded to the cassette inlet and a patient tube is bonded to the cassette outlet.

4. The pump of claim 3, in which the pump chamber is formed by bonding the two sheets together around an unbonded circular area and the flow path is formed between the pump chamber and the inlet and outlet by bonding the sheets along two spaced parallel lines extending from the circular area.

5. A pump for parenteral administration of fluid to a patient at a selectable rate comprising:
   A disposable element formed by a pair of substantially flat flexible plastic sheets and defining a supply chamber and a pump chamber located between an inlet and an outlet;
   an instrument body having a compartment for receiving the disposable element to confine the pump chamber;
   pumping means comprising a moveable hub circumferentially surrounded by radially extending petal-shaped sections, said pumping means associated with the instrument body adjacent to the compartment for confining the pump chamber, the hub and petal-shaped sections for movement toward and away from the pump chamber to vary the volume of the pump chamber;
   outlet valve closure means for closing the pump chamber outlet;
   refill means for pressing the supply chamber to refill the pump chamber and for withdrawing from the supply chamber to refill the supply chamber; and
   activation means for, during first time periods, simultaneously activating the pumping means to gradually reduce the volume of the pump chamber at a constant rate dependent upon the selected administration rate and activating withdrawal of the refill means to cause filling of the supply chamber and, during second time periods, activating the outlet valve closure means and simultaneously activating the pumping means to rapidly expand the volume of the pump chamber and activating the refill means to rapidly empty fluid from the supply chamber into the pump chamber.

6. For use with a parenteral administration pump body having a compartment formed by a rigid compartment wall opposed to a circular petal assembly having a hub circumferentially movable toward and away from the rigid wall, and radially extending petal-shaped sections each of which is pivotally mounted to the hub at its inner end and to a portion of the instrument body at its outer end so that the hub may be moved toward the rigid compartment wall to reduce the volume of the compartment, a disposable pump chamber element comprising:
   a first flexible and substantially flat sheet;
   a second flexible and substantially flat sheet bonded to the first sheet;
   a narrow inlet passage formed between the sheets by bonding of the first and second sheets along spaced parallel lines;
   a narrow outlet passage formed between the sheets by bonding of the first and second sheets along spaced parallel lines; and a pump chamber between the sheets communicating with the inlet and outlet having a diameter at least as large as the diameter of the petal assembly whereby fluid entering the inlet at a pressure of ten inches of water while the outlet is closed will fill the pump chamber and cause the chamber to bulge to a volume at least equal to the volume of the compartment in the pump body with the petal assembly fully retracted.

7. A pump for pumping a fluid to a patient comprising:

a disposable cassette formed by first and second flexible sheets defining a pump chamber therebetween, the pump chamber being variable in volume, said cassette further having an inlet passage for movement of fluid into the pump chamber and an outlet passage for movement of fluid out of the pumping chamber;

means for confining movement of the external surface of the first sheet;

a pumping member for contacting the external surface of the second sheet to deform the second sheet to decrease the volume of the pump chamber and pump fluid from the pump chamber, the pumping member including a center hub section and individual petal-shaped sections, each of said petal-shaped sections pivotally attached to the center hub section and extending radially outward from the center section;

support means for supporting each of the petal-shaped sections at their radially outward most extent for pivotal motion relative to said support means; and means for urging the hub section of the pump member towards the first sheet, causing the petal-shaped sections to pivot, the center hub section and petal-shaped sections being urged against the second sheet over substantially the entire surface area of the second sheet adjacent the pump member to decrease the volume of the pumping chamber and pump the fluid therefrom.

8. The infusion pump of claim 7 wherein said means for confining comprises a concave curved surface of constant radius against which the external side of the first sheet is confined.

9. The infusion pump of claim 7 wherein the disposable cassette further includes a supply chamber defined between the two sheets upstream from the pumping chamber, the inlet passage entering the supply chamber, said disposable cassette further having an intermediate passage interconnecting the supply chamber and pumping chamber.

10. The infusion pump of claim 7 further comprising an inlet valve operable between first and second positions for closing the inlet passage while in the first position to prevent fluid flow into the pumping chamber and opening the inlet passage to permit fluid flow to the pumping chamber in the second position; and a delivery valve for opening and closing the outlet passage so that the outlet valve opens to permit fluid flow from the pumping chamber through the outlet valve to the patient when the movement of the pump pressurizes the fluid at a predetermined pumping pressure.

11. The infusion pump of claim 10 wherein said infusion pump further includes means for sensing the fluid pressure in the pumping chamber, said outlet valve including an electronic control responsive to the fluid pressure measured by said pressure sensing means to control the opening of the outlet valve to maintain pressure in the pump chamber at a preselected pumping pressure.

12. The infusion pump of claim 10 wherein said pressure sensing means further senses an occlusion by sensing elevation of the fluid pressure in the pumping chamber above a predetermined maximum pumping pressure as the pump decreases the volume of the pumping chamber.

13. The infusion pump of claim 12 wherein the predetermined maximum pumping pressure is variable, whereby at low flow rates a reduced predetermined pumping pressure can be used to provide rapid sensing of an occlusion.

* * * * *